US012690837B2

(12) United States Patent
Sørensen

(10) Patent No.: US 12,690,837 B2
(45) Date of Patent: Jul. 28, 2026

(54) ENDOSCOPE

(71) Applicant: AMBU A/S, Ballerup (DK)

(72) Inventor: Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 231 days.

(21) Appl. No.: 18/210,882

(22) Filed: Jun. 16, 2023

(65) Prior Publication Data

US 2023/0404524 A1     Dec. 21, 2023

(30) Foreign Application Priority Data

Jun. 17, 2022     (EP) ..................................... 22179540

(51) Int. Cl.
| | |
|---|---|
| *A61B 8/12* | (2006.01) |
| *A61B 1/00* | (2006.01) |
| *A61B 1/005* | (2006.01) |
| *A61B 1/05* | (2006.01) |
| *A61B 1/06* | (2006.01) |
| *A61B 8/00* | (2006.01) |

(52) U.S. Cl.
CPC .............. *A61B 8/12* (2013.01); *A61B 1/0011* (2013.01); *A61B 1/0055* (2013.01); *A61B 1/05* (2013.01); *A61B 1/0676* (2013.01); *A61B 8/44* (2013.01); *A61B 8/4411* (2013.01); *A61B 8/4416* (2013.01); *A61B 8/445* (2013.01); *A61B 8/461* (2013.01); *A61B 1/00082* (2013.01)

(58) Field of Classification Search
CPC ....... A61B 8/445; A61B 8/12; A61B 1/00101; A61B 1/00105; A61B 1/00137; A61B 1/0125
See application file for complete search history.

(56) References Cited

U.S. PATENT DOCUMENTS

| | | | |
|---|---|---|---|
| 5,105,819 A | 4/1992 | Wollschlager et al. | |
| 7,449,004 B2 | 11/2008 | Yamada et al. | |
| 10,363,014 B1 * | 7/2019 | Steinberg ........... | A61B 1/00133 |
| 2002/0062084 A1 * | 5/2002 | Ohara ................ | A61B 1/00082 600/462 |
| 2009/0005689 A1 | 1/2009 | Kodama et al. | |
| 2010/0004509 A1 | 1/2010 | Naito et al. | |
| 2013/0137990 A1 * | 5/2013 | Tsuruta .............. | A61B 1/00087 600/466 |
| 2013/0331734 A1 | 12/2013 | Keast et al. | |
| 2015/0209005 A1 | 7/2015 | Bezanson et al. | |
| 2016/0051222 A1 * | 2/2016 | Imahashi ............. | A61B 8/4494 600/462 |

(Continued)

FOREIGN PATENT DOCUMENTS

| | | | | |
|---|---|---|---|---|
| KR | 20220008424 A | * | 1/2022 | ........... A61B 8/4422 |
| WO | 2021/067325 A1 | | 4/2021 | |
| WO | 2021/247418 A1 | | 12/2021 | |

OTHER PUBLICATIONS

European Search Report for EP Patent Application No. 22179540.4, Issued on Nov. 28, 2022, 8 pages.

*Primary Examiner* — Colin T. Sakamoto

(74) *Attorney, Agent, or Firm* — Faegre Drinker Biddle & Reath LLP

(57) ABSTRACT

An endoscope comprising a tip part having an ultrasound transceiver, a camera module, and a working channel. The tip part comprises an outer housing receiving the ultrasound transceiver and the camera module.

15 Claims, 9 Drawing Sheets

(56)　　　　　　References Cited

U.S. PATENT DOCUMENTS

| | | | | |
|---|---|---|---|---|
| 2016/0150947 A1* | 6/2016 | Marmor | .................. | A61B 1/06 |
| | | | | 600/110 |
| 2017/0007103 A1* | 1/2017 | Hashiguchi | ............ | A61B 1/018 |
| 2017/0007217 A1 | 1/2017 | Keast et al. | | |
| 2017/0049415 A1* | 2/2017 | Tsuruta | .................. | A61B 5/683 |
| 2017/0086802 A1* | 3/2017 | Mamiya | ................. | A61B 1/009 |
| 2017/0238807 A9 | 8/2017 | Vertikov | | |
| 2018/0042451 A1 | 2/2018 | Cuscuna et al. | | |
| 2018/0140175 A1 | 5/2018 | Luria et al. | | |
| 2019/0082937 A1* | 3/2019 | Hayashi | ................. | A61B 1/005 |
| 2019/0117192 A1 | 4/2019 | Saiga | | |
| 2019/0239726 A1* | 8/2019 | Hiraoka | ................. | A61B 1/018 |
| 2019/0282070 A1 | 9/2019 | Vilhelmsen et al. | | |
| 2020/0107708 A1* | 4/2020 | Amano | ..................... | A61B 8/12 |
| 2020/0178771 A1* | 6/2020 | Kolberg | ................. | A61B 1/018 |
| 2020/0288953 A1* | 9/2020 | Sørensen | ............. | G02B 23/243 |
| 2020/0323419 A1 | 10/2020 | Okada et al. | | |
| 2021/0169312 A1* | 6/2021 | Morimoto | ................ | A61B 8/12 |
| 2021/0321994 A1 | 10/2021 | Fleury et al. | | |
| 2021/0369239 A1* | 12/2021 | Isobe | .................... | B06B 1/0633 |
| 2021/0393113 A1 | 12/2021 | Matthison-Hansen | | |
| 2022/0117462 A1 | 4/2022 | Hansen et al. | | |
| 2022/0233054 A1 | 7/2022 | Hansen et al. | | |
| 2022/0338812 A1* | 10/2022 | Duval | ............... | A61B 1/00154 |
| 2022/0409175 A1* | 12/2022 | Kinomoto | ................ | A61B 8/12 |
| 2022/0409177 A1 | 12/2022 | Morimoto | | |
| 2023/0000317 A1* | 1/2023 | Steinberg | ............ | A61B 8/4466 |
| 2023/0016068 A1 | 1/2023 | Sato et al. | | |
| 2023/0018150 A1* | 1/2023 | Miyagishima | ..... | A61B 1/00073 |
| 2023/0122213 A1* | 4/2023 | Harada | .................... | A61B 8/12 |
| | | | | 600/471 |
| 2024/0237967 A1* | 7/2024 | Steinberg | ................. | A61B 8/08 |

* cited by examiner

ENDOSCOPE

CROSS-REFERENCE TO RELATED APPLICATIONS

This application claims priority from and the benefit of European Patent Application No. EP22179540.4, filed Jun. 17, 2022, which is incorporated by reference herein in its entirety.

TECHNICAL FIELD

The present disclosure relates to endoscopes, in particular but not exclusively to disposable EndoBronchial UltraSound endoscopes, normally abbreviated with the acronym EBUS endoscopes.

BACKGROUND

Like many other endoscopes, EBUS endoscopes comprise a proximal handle from which an insertion cord extends. The insertion cord normally comprises a bendable main tube connected to a highly flexible bending section. The bending section normally comprises a number of segments connected by hinge members so as to allow it to be articulated. The distal end of the bending section, in turn, is connected to a tip member with features providing desired functionalities such as illumination, vision, exit ports for tools, liquid instillation, fluid insufflation, suction etc. In EBUS endoscopes one of the features is an ultrasound transceiver allowing to look into the tissue, for example behind the bronchial wall. Furthermore, in EBUS endoscopes, the tip member may comprise attachment features, such as grooves, for the attachment of a balloon surrounding the ultrasound transceiver. The balloon may then be filled with liquid from a port in the tip part so as to provide a good match of acoustic impedance to the surrounding tissue that is to be ultrasoundally probed. The proximal handle is adapted to be gripped by a hand of an operator. The handle may comprise an operating member allowing control of the bending section, so that the insertion cord may be manoeuvred during insertion into a patient e.g. into the bronchia.

In order to keep manufacturing costs low to allow the endoscope to be disposable it is important to devise a tip part in which it is easy to accommodate and precisely locate the separate parts for providing inter alia the functionalities mentioned above.

SUMMARY

According to a first aspect of the disclosure, an embodiment of an endoscope comprises a handle and an insertion cord comprising a tip part. The tip part includes an ultrasound transceiver and a camera module.

This allows the tip part to be made modular, in turn allowing prefabrication and testing of the parts of the inner housing and parts accommodated separately elsewhere in the outer housing.

According to a second aspect of the disclosure, an embodiment of a tip part includes an outer housing receiving a camera module and an ultrasound transducer module.

According to a third aspect of the disclosure, the object is achieved by a method in assembling an endoscope, said method comprising manufacturing a first housing having a working channel passage, accommodating in said housing a camera, placing and securing said first housing in a second, outer housing, joining the outer housing with the remainder of the endoscope.

According to a fourth aspect of the disclosure, the object is achieved by a system comprising a display device and an endoscope according to the first aspect of the disclosure, connectable to said display device.

According to variation of the first embodiment, the inner housing further comprises the working channel. This aids in ensuring proper alignment between the working channel and the camera, in turn allowing both to be easily placed in the correct orientation with respect to the overall tip part.

According to variation of the first embodiment, the outer housing comprises guide structure adapted to receive and hold the inner housing in a predetermined orientation with respect to the outer housing. This further facilitates the correct angular positioning of the camera and working channel.

According to variation of the first embodiment, the inner housing comprises a prefabricated integrally moulded two-component housing. This has shown to be an efficient way of making a unit with both a camera and a working channel in a predetermined alignment with the camera, as well as facilitating the provision of transparent windows in front of the camera and illumination components.

The ultrasound transceiver is located between the camera module and the distal end of the endoscope. This allows the ultrasound transceiver to have a sideways view with respect to the longitudinal axis C-C of the endoscope, without obstructing the more forward view of the vision camera and vice versa.

According to variation of the first embodiment, the outer housing comprises guide structure adapted to receive and hold the inner housing in a predetermined orientation with respect to the outer housing. This facilitates the correct angular positioning of the camera and working channel.

According to an embodiment of the second aspect of the disclosure, the inner housing comprises a prefabricated integrally moulded two-component housing. This has shown to be an efficient way of making a unit with both a camera and a working channel in a predetermined alignment with the camera, as well as facilitating the provision of transparent windows in front of the camera and illumination components.

According to variation of the first embodiment, the outer housing comprises one or more grooves provided in an outer surface of said outer housing and adapted for receiving a balloon. Providing a groove allows a balloon to be placed around the ultrasound transceiver. Filling the balloon with a fluid such as a aqueous saline solution provides good acoustic impedance match between the tissue and the ultrasound transceiver so as to reduce reflections at transition surfaces.

According to variation of the first embodiment, said outer housing comprises a fluid passage adapted for fluid passage to said balloon. Providing the fluid passage allows the balloon to be filled with fluid independently of the remainder of the tip.

According to variation of the first embodiment, the first housing is manufactured with a working channel passage. This provides a first inner housing which aids in ensuring proper alignment between the working channel and the camera, in turn allowing both to be easily placed in the correct orientation with respect to the overall tip part.

According to variation of the first embodiment, the first housing is inserted into a guide structure in said outer housing adapted to receive and hold the first housing in a predetermined orientation with respect to the outer housing.

According to an embodiment according to the third aspect of the disclosure, the first housing comprises a prefabricated integrally moulded two-component housing. This has shown to be an efficient way of making a unit with both a camera and a working channel in a predetermined alignment with the camera, as well as facilitating the provision of transparent windows in front of the camera and illumination components.

Variations of embodiments may be combined such that two or more variations are present, when appropriate.

BRIEF DESCRIPTION OF THE DRAWINGS

The disclosure will now be made in greater detail based on non-limiting exemplary embodiments and with reference to the drawings, on which.

DETAILED DESCRIPTION

Figure 1:
FIG. 1 shows a system comprising a display device and an EBUS bronchoscope connectable to the display device.

Turning first to FIG. 1, a viscualization system 1 comprises a display unit 2 to which an endoscope 3 is connectable as indicated by the dashed double arrow 4. The endoscope 3 is preferably an EBUS endoscope and is thus also connectable to an ultrasound control device 5 adapted to generate electrical signals to an ultrasound transceiver 6 and to receive electrical signals from the ultrasound transceiver 6 as indicated by the double arrow 7. The connections and configurations shown are examples. For example, connections from the endoscope 3 to the display unit 2 may be via the ultrasound control device 5 or vice versa. The display unit 2 may serve to display both visual images and ultrasound images from the endoscope 3 or the ultrasound control device 5 may have a dedicated screen for the ultrasound images, be it integrated or as a separate screen.

Figure 4:
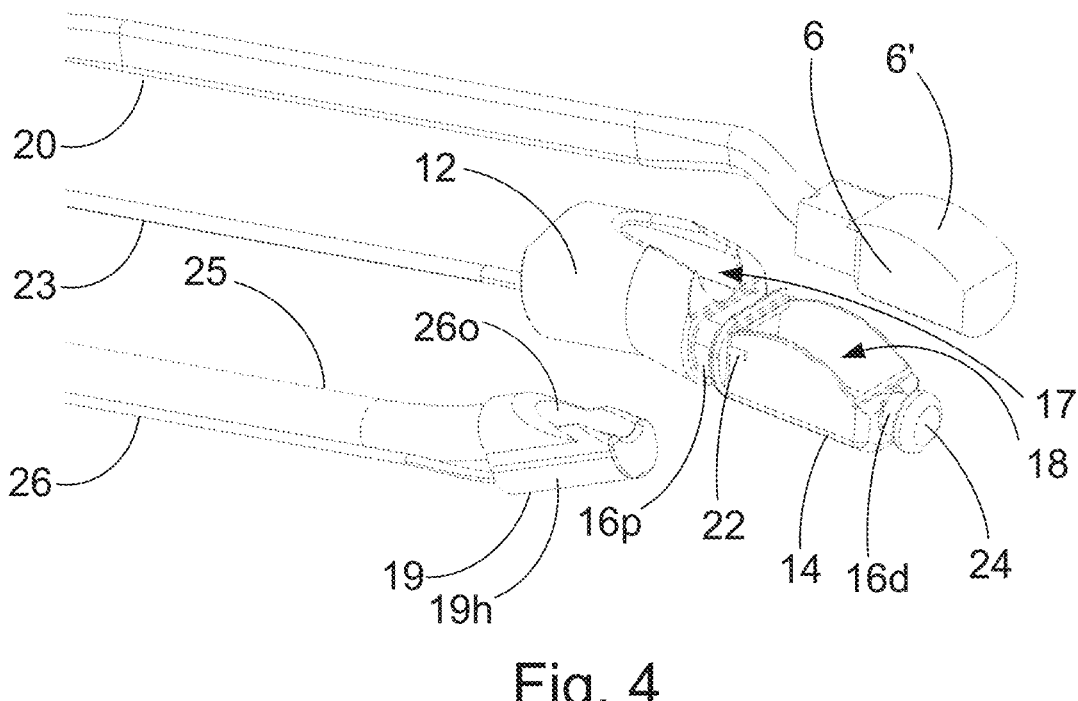
FIG. 4 shows an exploded view of the tip part.

The endoscope 3 comprises a handle 8 forming the proximal end of the endoscope 3. From the handle an insertion cord extends, the insertion cord comprising a main tube 9, a bending section 10 and a tip part 11. The main tube 9 extends from the distal end of the handle 3 and defines a longitudinal axis C-C for the endoscope. The bending section 10 is connected to the distal end of the main tube 9. Compared to the main tube 9, the bending section is highly bendable, e.g. by comprising a number of articulated segments. The tip part 11 is connected to the distal end of the bending section 10, e.g. to the distal end segment if the bending section comprises multiple articulated segments. An exploded view of the tip part 11 is shown in FIG. 4.

Figure 2:
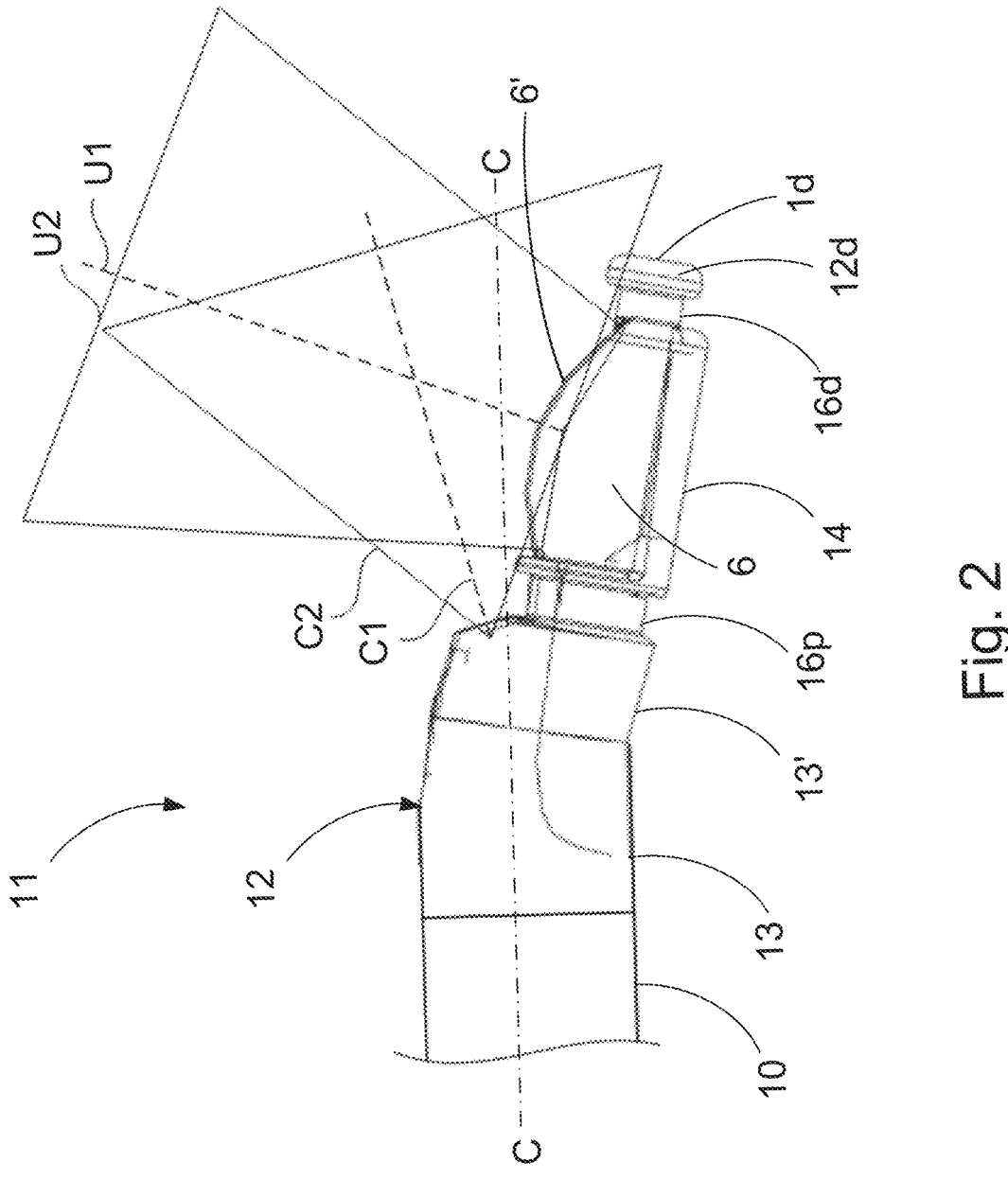
FIG. 2 shows a side view of an outer tip housing of the EBUS bronchoscope.
Figure 3:
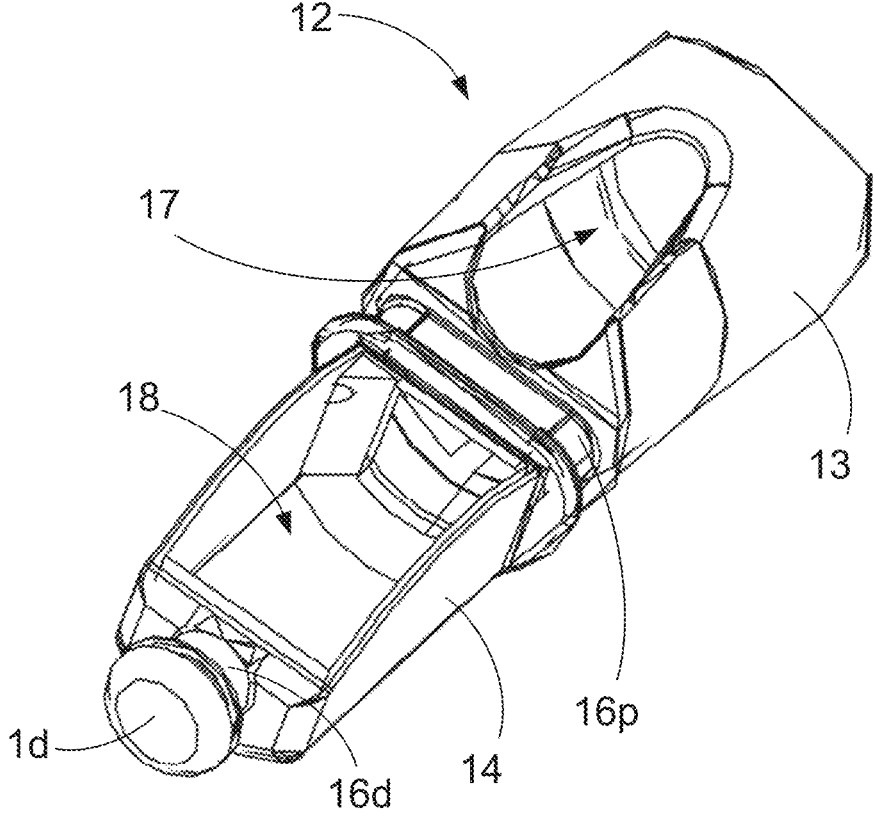
FIG. 3 shows a front isometric view of the outer tip housing of FIG. 2.

Turning now to FIGS. 2 and 3, an outer housing 12 of the tip part 11 is shown in side view. The outer housing 12 is preferably moulded as a single piece item from a polymer material in a suitable process, such as injection moulding. The outer housing 12 comprises a proximal portion 13 adapted for connection to the bending section 10 and comprises a recess adapted for receiving a camera module 19 comprising an inner housing 19h (or housing) and a camera. A distal portion 14 comprises a recess adapted for accommodating the ultrasound transceiver 6, providing a first, or ultrasound transceiver, compartment 18 (see FIG. 3). Optionally, an angled section 13', has some inclination away from the longitudinal axis C-C, of the proximal portion 13 may be provided proximal of the distal portion 14. The distal portion 14 is inclined away from the longitudinal axis C-C (downward in the orientation shown in FIG. 2) with respect to the proximal portion 13, which is generally aligned with the longitudinal axis C-C in order to provide a good mechanical connection to the bending section 10. The ultrasound transceiver 6 is preferably accommodated between the camera module 19 and the distal end 1d of the endoscope 1. The emission surface 6' of the ultrasound transceiver 6 is preferably curvilinear and is preferably arranged so that emission and reception is generally sideways and only slightly forward with respect to the longitudinal axis C-C of the endoscope 1. In the illustrated embodiment, the center U1 of the emission and reception cone U2 is at an angle of about 70° to the longitudinal axis C-C of the endoscope 1. The angle may be in a range between 60° and 80°. The camera is more forward looking and less sideways looking. In the illustrated embodiment, the center C1 of the field of view C2 is arranged at an angle of about 20° with respect to the longitudinal axis C-C of the endoscope 1. The angle may be in a range between 30° and 45°. This arrangement prevents the camera and ultrasound transceiver visual and acoustic fields of view, respectively, from obstructing each other.

A pair of circumferential grooves 16p, 16d, for receiving a sleeve like balloon surrounding the ultrasound transceiver 6 in use, are preferably also provided in the outer housing 12. As shown, the proximal groove 16p is positioned intermediate the camera module 19 and the untrasonic transceiver 6. In this context by untrasonic transceiver it is meant to portion that emits and receives ultrasound waves and not the cables and optional components used to transmit ultrasound signals to the handle of the endoscope. As shown, the proximal groove 16p is between the proximal portion 13 and the ultrasound transceiver 6. Beyond the most distal groove 16d, a small lump 12d, having a cross-section larger than the cross-section of the outer housing where the distal groove 16d is formed, forms the distal end 1d of the tip part 11 and of the endoscope 3. Using a pair of circumferential grooves 16p, 16d is, however, only a preferred embodiment, and embodiments where the balloon engages only a single groove are also envisaged. The balloon may be filled with a suitable media such as an aqueous saline solution in order to match the acoustic impedance to the tissue into which the ultrasound is emitted and from which it is received back.

Referring to FIG. 3, apart from being adapted for connection to the bending section 10, the proximal portion 13 of the tip part 11 furthermore comprises a first, or camera module, compartment 17 adapted to receive a camera module 19 (see FIG. 5) and a second, or ultrasound transceiver, compartment 18 adapted to receive the ultrasound transceiver 6.

FIG. 4 is an exploded view of the tip part 11 showing, separately, the ultrasound transceiver 6, the camera module 19, and the outer housing 12. A working channel outlet 26o is positioned above the camera module 19 (above refers to the position on the page). Cables 20 extend from the ultrasound transceiver 6 to the handle 8 and are provided to transmit signals to and from the ultrasound transceiver 6. The signals include ultrasound signals received by the ultrasound transceiver 6. The outer housing 12 includes a balloon fill channel 22 that is in fluid connection with an fill tube 23 leading though the main tube 9 and the handle 3 to a fluid inlet (not shown) at a suitable location, such as in the handle 8. The camera module 19 in the present embodiment is in fluid connection with a working channel tube 25. Cables 26 extend from the camera module 19 to the handle 8 and are provided to transmit signals to and from the camera module 19 and power. The signals may comprise configuration signals and image data signals configured to transmit data representing images captured by an image sensor of the camera of the camera module 19. The camera module 19 may include light emitters, such as light emitting diodes or distal ends of light conducting fibers. The power cables also supply power to light emitting diodes.

In one variation of the present embodiment, the camera module 6 includes a housing and a camera positioned inside the housing, the camera module being capable of generating images prior to insertion into the camera module compartment. In this manner the camera module can be connected to a monitor configured to receive the image data to test and ensure the camera module is functioning properly before it is attached to the outer housing 12. If the camera module 19 is defective in any way, it can be discarded without having to discard the entire tip part 11. The ultrasound transceiver 6 may also be tested before it is assembled in the outer housing 12 to achieve the same benefits.

Figure 5:
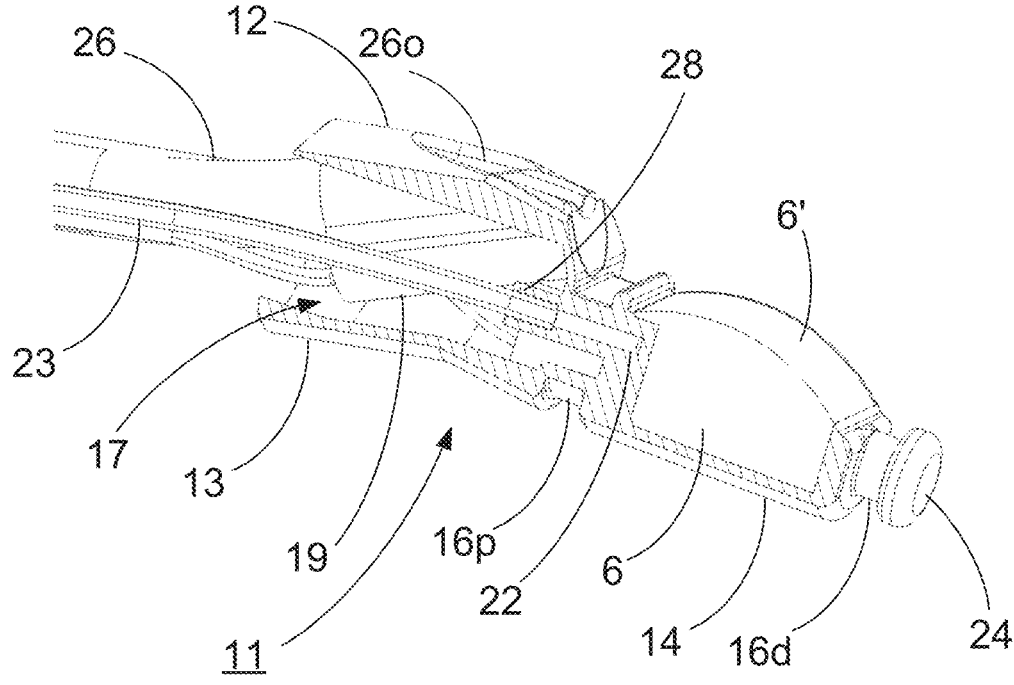
FIG. 5 shows a cross-sectional view of the outer tip housing of FIG. 2.

FIG. 5 is a sectioned view of the tip part 11 showing the camera module 19 positioned in the camera module compartment 17 and the ultrasound transceiver 6 positioned in the ultrasound transceiver compartment 18. The tip part 11 is sectioned along a plane traversing the fill tube 23. As shown, the fill tube 23 is inserted into a cavity in an optional protruding portion 28 of the outer housing 12 located in the camera module compartment 17. The balloon fill channel 22 extends distally from the distal end of the fill tube 23 and from the proximal groove 16p. The protruding portion 28 may be omitted, in which case the cavity can be positioned further distally in the outer housing 12.

Figure 6:
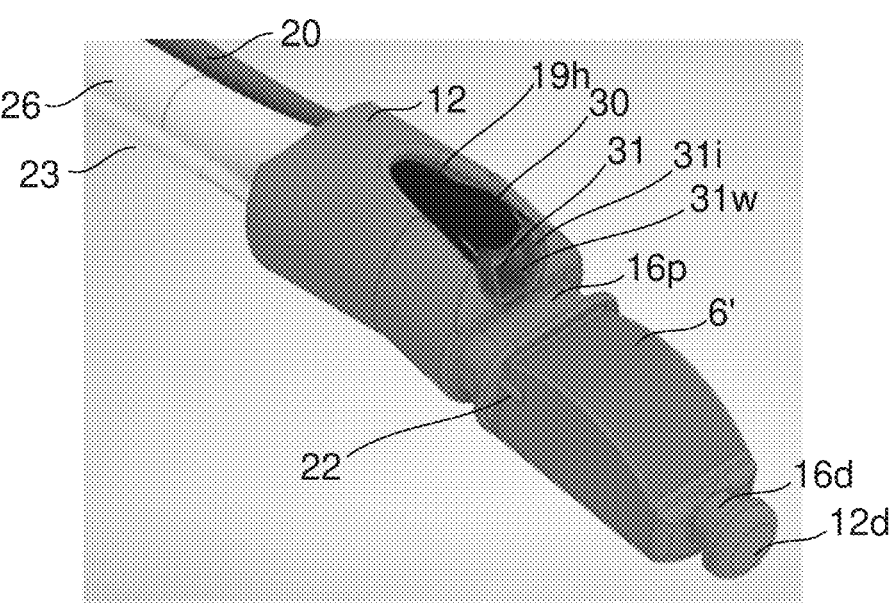
FIG. 6 is perspective view of the assembled distal tip part.

FIG. 6 is perspective view of the assembled tip 11 showing the camera module 19 positioned in the camera module compartment 17 and the ultrasound transceiver 6 positioned in the ultrasound transceiver compartment 18. The tip part 11 is sectioned along a plane traversing the fill tube 23. As shown, the fill tube 23 is inserted into a cavity in an optional protruding portion 28 of the outer housing 12 located in the camera module compartment 17. The balloon fill channel 22 extends distally from the distal end of the fill tube 23 and from the proximal groove 16p. The protruding portion 28 may be omitted, in which case the cavity can be positioned further distally in the outer housing 12. The housing 19h may comprise an opaque portion 30 and a transparent portion 31. The transparent portion 31 comprises a viewing window 31w and a pair of illumination windows 31i. The opaque and transparent portions may be formed separately and then bonded to form the housing 19h. Alternatively, the opaque and transparent portions may be injection molded in a two-stage process in which one of the two parts is formed first and then the other portion is molded so that the heat of the polymer material fuses to the already formed portion, thus providing a housing formed in one piece.

Figure 7:
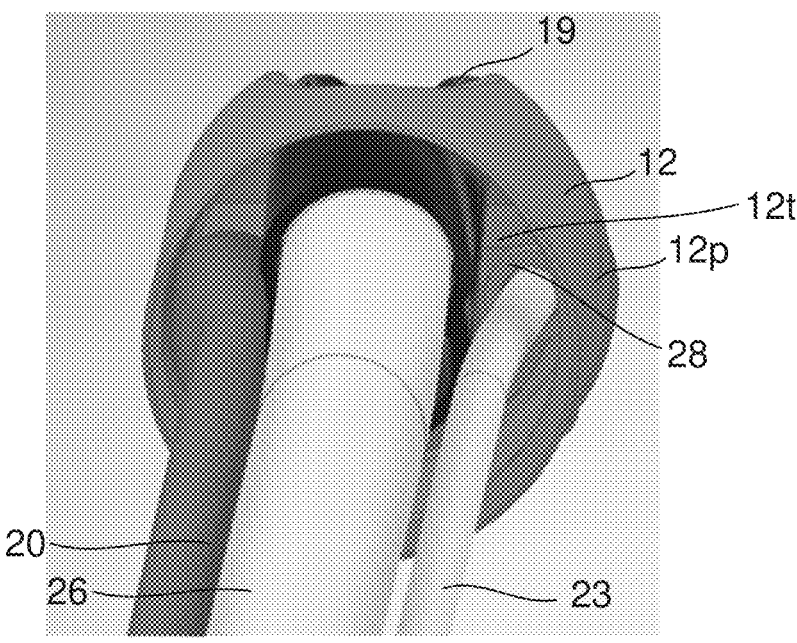
FIG. 7 is proximal view of the assembled tip part.

FIG. 7 is view of the assembled tip part 11 from the proximal side. As shown, the outer housing 12 has a peripheral wall 12 and a proximal surface 12t that is transverse to the longitudinal axis of the outer housing 12. The fill tube 23 and the cables 20 extend proximally on either side of the working channel tube 26. The camera is positioned below the working channel tube 26.

Figures 8, 9:
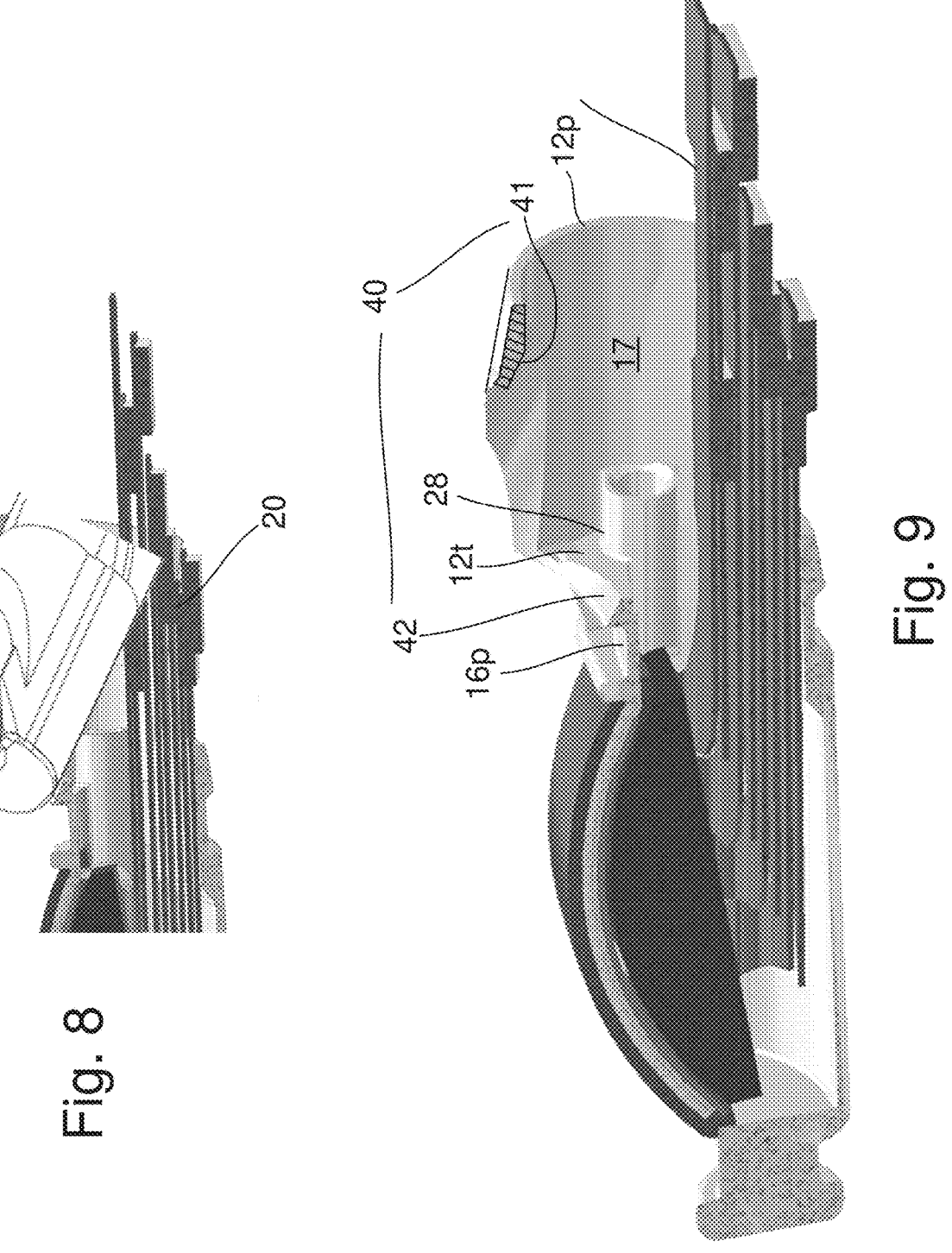
FIG. 8 depicts a camera module positioned in the outer housing.
FIG. 9 is like FIG. 8 but with the camera module removed.

FIG. 8 depicts the camera module 6 positioned in the camera module compartment 17. FIG. 9 is like FIG. 8 but with the camera module 6 removed. The tip part 11 preferably comprises one or more guide structures 40 to ensure the proper orientation of the camera module 19. In one variation, guide structures 40 comprise guide surfaces 41 and 42 which are molded in the outer housing 12, as shown in FIG. 9. Guide structures 41 and 42 are guide surfaces parallel to the peripheral surface of the housing 19h when the camera module 19 is in position. As camera modules change over time, some becoming smaller, some without working channels, for example, or different views are desirable for specialized procedures, the outer housing 12 can be molded with guide surfaces more or less spaced apart, or at different angles, to accommodate such variations. Thereby, for the relatively small cost of the outer housing 12, the outer housing 12 can be redesigned to construct a different tip part 11. Furthermore, the same camera module 19 may be used in other endoscopes, without ultrasound transceivers, thereby enabling reductions in manufacturing work-in-process and inventory.

Figure 10:
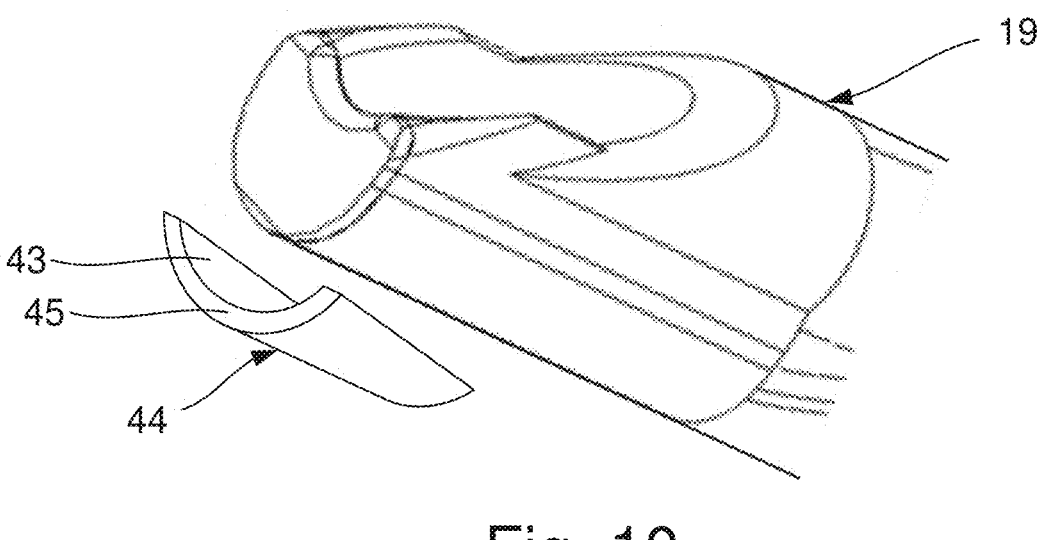
FIGS. 10 and 11 illustrate guide structures.
Figure 11:
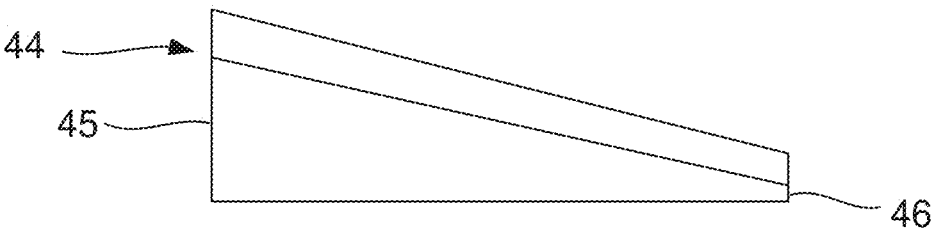

In another variation, shown in FIGS. 10 and 11, guide structures 40 comprise guide surfaces 41 and 42 which are molded in separate parts, for example wedge part 44. FIG. 11 is a schematic view of an insert part 44. The insert part 44 is shaped as a wedge and has a thicker front 46 than rear 46, thus enabling elevation of the field of view without modifying the outer housing 19. The insert part 44 may be bonded to the camera module 19 or to the outer housing 12 before insertion of the camera module 19 into the outer housing 12. Thusly, guide structures ensure the proper orientation of the camera. The insert part can be substituted with a small part that increases a gap between the camera module 19 and the outer housing 12 at points of contact therebetween, such as surfaces 41 and 42, which is not necessarily wedge shaped. Thus, generally, these guide structures 40 can be considered housing inserts.

The camera module 19 includes a camera positioned inside the inner housing, or housing, and, optionally, a fluid connector for connection to a working channel tube. The camera module may be prefabricated so that a given alignment between the working channel, in particular the exit port thereof, and the camera is ensured prior to final assembly. This can be achieved by arranging the working channel, the camera and possibly illumination sources in the inner housing 19h. As described above and below, the housing 19h can comprising a prefabricated integrally moulded two-component housing. Whether the illumination sources are also within the inner housing may inter alia depend on whether they are provide as light emitting diodes, e.g. LEDs, or as emission ends of light fibres to which light is fed at an opposite light reception end, e.g. from external primary light sources or from primary light sources in the handle. It may, however, also be possible to provide the inner housing without the integrated working channel and provide the working channel separately. This could be done using processes corresponding to the manufacture of an entire tip housing known from U.S. Publication No. 2019/0282070 but with smaller dimensions as no space for pull-wires will be needed, and therefore allow the inner housing 19*h* to fit well within the outer housing 12. The inner housing 19*h* may, however, also be moulded around the relevant parts once they are properly aligned in the prefabrication process. The working channel in the camera module 19 is adapted to be connected a working channel tube 26 running through the insertion cord to an entry port at a suitable location in the handle 8.

Figure 12:
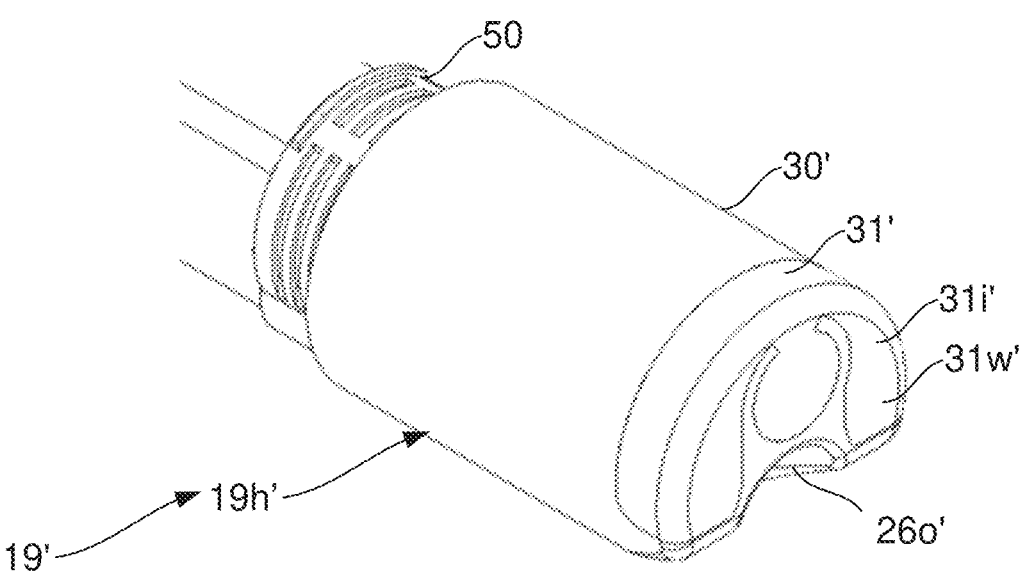
FIGS. 12 to 15 illustrate another embodiment of a camera module.
Figure 13:
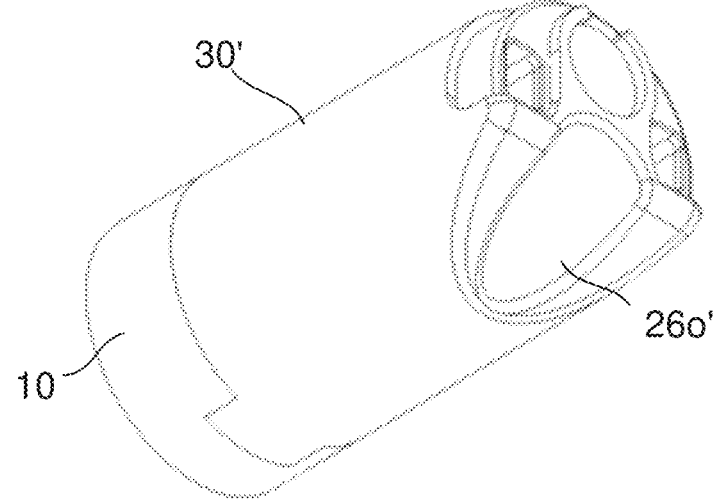
Figure 14:
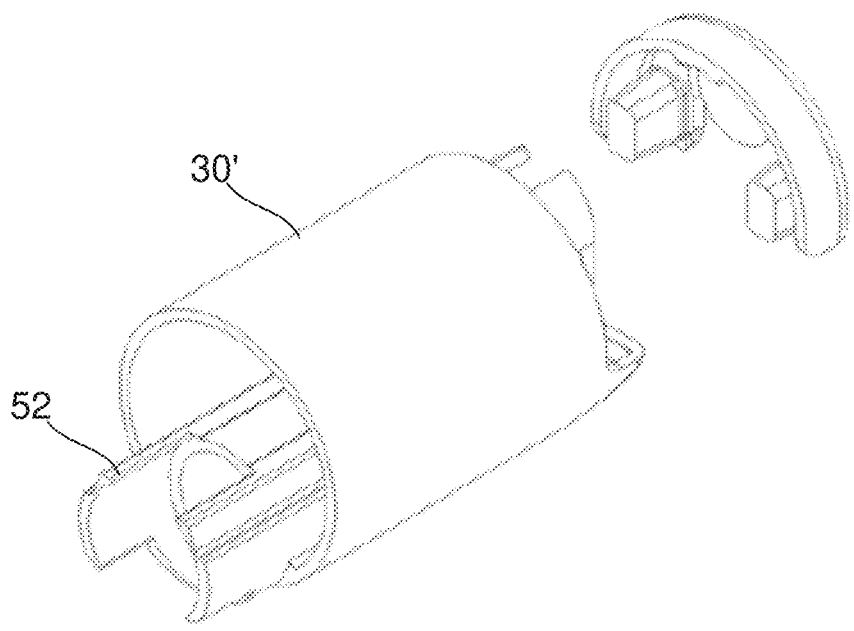

FIGS. 12 to 14 depict a camera module known from U.S. Publication No. 2019/0282070, which describes a commonly-owned patent application that is incorporated herein by reference in its entirety. The internal components of such module can be used with the camera module 19, with some modifications. Alternatively, instead of an image sensor a miniature camera can be used which incorporates lenses and an image sensor, for example. The camera module housing depicted in these figures is made by the two-stage molding process mentioned above. Where parts have corresponding functions, same numbers are used, with the addition of apostrophes. Referring to FIGS. 12 and 13, the camera module 19' includes a proximal attachment portion 50 configured to secure the housing 19*h* to the bending section 10. The camera module 19 does not require the proximal attachment portion 50 because it is not attached directly to the bending section 10. Insteady, the proximal attachment portion 50 can be secured to the outer housing 12 so that it can be secured to the bending section 10. Otherwise, camera module 19' can be used with the outer housing 12 to form the tip part 11.

Figure 15:
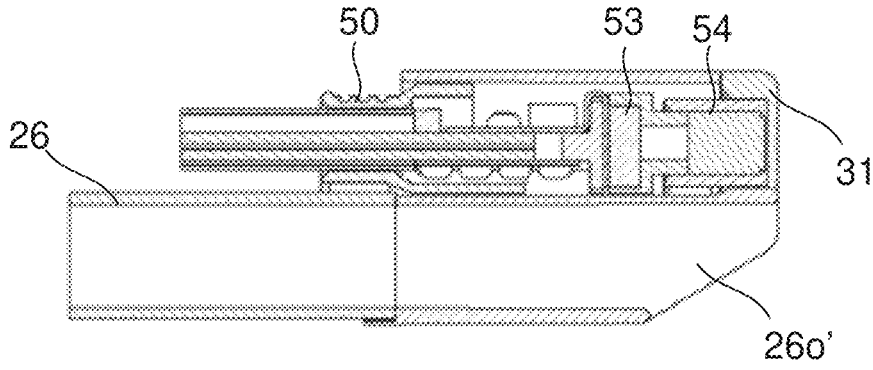

FIG. 14 illustrates a pair of walls 52 provided to secure the working channel tube 26 to the housing 19*h*'. The walls 52 are molded with the opaque portion 30. FIG. 15 illustrates components of the camera module 19 including an image sensor 53 and a barrel 54 containing lenses. Other components include a circuit board and a pair of LEDs.

With the parts described above an endoscope may easily be assembled in manufacture from these prefabricated parts and assemblies. This would involve, manufacturing the first housing having a working channel passage and accommodating a camera in the first housing. The first housing may then be placed and secured in a preferably prefabricated second, outer, housing. The ultrasound transceiver is positioned in the outer housing in the same manner. Upon this the tip part now comprising both first and second housings may be joined with the remainder of the endoscope, e.g. by connecting the second housing to the bending section.

A positioning interface, or interface, functions to control the position of the insertion cord. The handle 8 is an example of a positioning interface and, unless stated otherwise, the terms are used interchangeably. The positioning interface also functions to provide the steering controls, e.g. knobs, levers, buttons, and the like, to steer the field of view of the camera and the elevator controls. Alternatively, a different positioning interface can be provided that is connected to the insertion cord and is detachably connected to a robotic arm. The insertion cord thus extends from the robotic arm, and the intrusive medical device is detachable from the robotic arm. The robotic arm responds to signals, including voice commands from an operator, to rotate, translate, and otherwise position the proximal end of the insertion cord, as an operator would do manually. The positioning interface can include control actuators, including manual control actuators. Alternatively or additionally, control actuators can be provided in or on the robotic arm or by the robotic system including the robotic arm, thereby potentially reducing the cost of the intrusive medical device. Example control actuators include single axis actuators, including linear motion actuators. A linear motion actuator may comprise a threaded rod coupled to a threaded nut portion, in which a motor rotates the rod to translate the nut portion.

The display unit 2 may also be referred to as a video processing apparatus (VPA) including a housing enclosing and supporting a display screen, a video processing circuit, and an endoscope interface configured to communicate with the camera module 19. The VPA allows an operator to view an image captured by the image sensor of the camera.

Variations of the VPA can be provided. For example, it might not be desirable to provide a video display screen with a touch screen, or it might be desirable to omit a display screen altogether. Omission of the display screen might be beneficial to take advantage of evolving video display technologies which improve resolution and reduce cost. Provision of exchangeable medical device interfaces allows for adoption of evolving image sensor and endoscope technologies, thus use of existing or future-developed external video displays could allow presentation of higher resolution or otherwise improved video. Use of external video displays could also leverage existing capital investments.

In all embodiments, the endoscope may be disposable and may not be intended to be cleaned and reused. Alternatively the endoscope may, in all embodiments, be re-usable. In some variations of the present embodiment, the endoscope and the VPA comprise wireless transceivers to exchange image data and configuration data. The endoscope may comprise a battery to power the image sensor and the LEDs.

The video processing circuit of the VPA is operable to receive image data, present a graphical user interface to allow a user to manipulate image data with a touch screen, and, optionally, output a video signal to allow remote viewing of the images presented with the touch screen. A separate, potentially remote, display screen may also be connected to the endoscope via the VPA, which may include or omit the display screen. Medical device interfaces include cable sockets and circuits to compatibilize the signals from the image sensors, for example. Thus, a particular type of endoscope is matched with a corresponding medical device interface and the VPA can thus enable use of different endoscope technologies. The medical device interfaces may also include isolation amplifiers to electrically isolate the video signal, and a power output connector to provide power to the endoscope for the image sensor and the LEDs. The medical device interfaces may also include a serial to parallel converter circuit to deserialize the video signals of endoscopes that generate serial signals, for example serial analog video signals. The medical device interfaces may also include a configuration connector to output image sensor configuration parameters such as image inversion, clock, shutter speed etc.

The following items are additional variations and examples of the embodiments described with reference to the figures:

1. An endoscope comprising a proximal handle, an insertion cord extending from said handle towards the distal end of the endoscope, said insertion cord comprises a tip part, where the tip part comprises an ultrasound transceiver, a camera, illumination source, and a working channel, wherein the tip part comprise an outer housing and an inner housing accommodated within the outer housing, said inner housing comprising the camera.

2. An endoscope according to item 1, wherein the inner housing further comprises the working channel.

3. An endoscope according to any one of items 1 or 2, wherein the outer housing comprises a guide structure adapted to receive and hold the inner housing in a predetermined orientation with respect to the outer housing.

4. An endoscope according to any one of the preceding items, wherein the inner housing comprises a prefabricated integrally moulded two-component housing.

5. An endoscope according to any one of the preceding items wherein the outer housing comprises one or more grooves provided in an outer surface of said outer housing and adapted for receiving a balloon.

6. An endoscope according to item 5, wherein said outer housing comprises a fluid passage adapted for fluid passage to said balloon.

7. An endoscope according to any one of the preceding items, wherein the outer housing comprises a compartment adapted to receive the ultrasound transceiver.

8. A tip part for an endoscope, said tip part comprising an outer housing part adapted to receive a camera module and an ultrasound transceiver, wherein the camera module is arranged in an inner housing accommodated in the outer housing.

9. A tip part for an endoscope, wherein the ultrasound transceiver is located between the camera module and the distal end of the endoscope.

10. A tip part according to any one of items 8 or 9, wherein the outer housing comprises a guide structure adapted to receive and hold the inner housing in a predetermined orientation with respect to the outer housing.

11. A tip part according to any one of items 8 to 10, wherein the inner housing comprises a prefabricated integrally moulded two-component housing.

12. A tip part according to any one of items 8 to 11, wherein the outer housing comprises one or more grooves provided in an outer surface of said outer housing and adapted for receiving a balloon.

13. A tip part according to item 12, wherein said outer housing comprises a fluid passage adapted for fluid passage to said balloon.

14. Method in assembling an endoscope, said method comprising manufacturing a first housing, accommodating in said first housing a camera, placing and securing said first housing in a second, outer housing, joining the outer housing with the remainder of the endoscope.

15. Method according to item 14, wherein the first housing is manufactured with a working channel passage.

16. A method according to any one of items 14 or 15, wherein the first housing is inserted into a guide structure in said outer housing adapted to receive and hold the first housing in a predetermined orientation with respect to the outer housing.

17. A method according to any one of items 14 or 16, wherein the first housing comprises a prefabricated integrally moulded two-component housing.

18. A system comprising one or more display devices, a control device for an ultrasound transceiver and an endoscope according to any one of items 1 to 7, connectable to said display device and said control device.

I claim:

1. An endoscope comprising:
a handle;
a main tube connected to the handle;
a bending section connected to the main tube; and

a working channel tube extending from the handle and inside the main tube and the bending section; and
a tip part connected to the bending section and comprising:
an outer housing comprising a single piece item including a proximal portion, a distal portion, a camera module compartment in the proximal portion, and an ultrasound transceiver compartment in the distal portion,
an ultrasound transceiver positioned in the ultrasound transceiver compartment, and
a camera module positioned in the camera module compartment and affixed to the outer housing,
wherein the camera module includes a housing and a camera positioned inside the housing, the camera module being capable of generating images prior to insertion into the camera module compartment, and
wherein the housing includes a working channel outlet and a distal working channel portion connected to the working channel tube to form a working channel extending from the handle to the working channel outlet.

2. The endoscope of claim 1, wherein the outer housing comprises a guide structure configured to secure the camera module in a desired orientation within the camera compartment.

3. The endoscope of claim 1, further comprising a guide structure comprising an insert part positioned adjacent the camera module between the camera module and a surface of the camera module compartment facing the camera module.

4. The endoscope of claim 1, wherein the housing of the camera module comprises a prefabricated housing formed in one-piece from two components fused together.

5. The endoscope of claim 1, wherein the outer housing comprises a groove configured to retain a balloon, wherein the outer housing comprises a fluid passage configured to receive a fluid and to discharge the fluid into the balloon, wherein the fluid passage has an outlet opening distal of the groove.

6. The endoscope of claim 5, wherein the groove is positioned intermediate the camera module and the ultrasound transceiver.

7. The endoscope of claim 1, wherein the ultrasound transceiver is located between the camera module and the distal end of the endoscope.

8. The endoscope of claim 1,
wherein the outer housing comprises a groove configured to retain a balloon, and
wherein the groove is positioned intermediate the camera module and the ultrasound transceiver.

9. A method of assembling the endoscope of claim 8, the method comprising:
manufacturing the outer housing;
inserting and securing the camera module in the outer housing;
inserting and securing the ultrasound transceiver in the outer housing;
providing a bending section; and
joining the outer housing to the bending section.

10. The method of claim 9, further comprising securing the working channel tube to the housing of the camera module before inserting and securing the camera module in the outer housing.

11. A visualization system comprising:
one or more display devices; and the endoscope of claim 8, the endoscope being configured to transmit images data for presentation with the one or more display devices.

12. A method of assembling the endoscope of claim 1, the method comprising:

manufacturing the outer housing;

inserting and securing the camera module in the outer housing;

inserting and securing the ultrasound transceiver in the outer housing;

providing a bending section; and joining the outer housing to the bending section.

13. The method of claim 12, further comprising securing the working channel tube to the housing of the camera module before inserting and securing the camera module in the outer housing.

14. The method of claim 12, further comprising bonding an insert part to the camera module before inserting and securing the camera module to the outer housing.

15. A visualization system comprising:

one or more display devices; and the endoscope of claim 1, the endoscope being configured to transmit images data for presentation with the one or more display devices.

* * * * *